United States Patent [19]

Okamoto et al.

[11] Patent Number: 5,420,144

[45] Date of Patent: May 30, 1995

[54] PYRIDYL SUBSTITUTED BENZOTHIAZOLE COMPOUNDS WHICH HAVE USEFUL PHARMACEUTICAL UTILITY

[75] Inventors: Yasushi Okamoto; Katsuya Tagami; Shigeki Hibi; Hirotoshi Numata; Naoki Kobayashi; Masanobu Shinoda; Tetsuya Kawahara; Manabu Murakami; Kiyoshi Oketani; Takashi Inoue; Takashi Yamanaka; Isao Yamatsu, all of Ibaraki, Japan

[73] Assignee: Eisai Co., Ltd., Tokyo, Japan

[21] Appl. No.: 148,914

[22] Filed: Nov. 5, 1993

Related U.S. Application Data

[62] Division of Ser. No. 861,379, Mar. 31, 1992, Pat. No. 5,300,518.

[30] Foreign Application Priority Data

Apr. 4, 1991 [JP] Japan ................................. 3-71480
Oct. 28, 1991 [JP] Japan ................................. 3-281366

[51] Int. Cl.$^6$ .................... C07D 417/04; A61K 31/41
[52] U.S. Cl. ................................. 514/338; 546/270
[58] Field of Search .......................... 546/270; 514/338

[56] References Cited

U.S. PATENT DOCUMENTS 1,931,077 10/1933 Lubs et al. ........................... 548/157
4,873,346 10/1989 Anderson ............................. 548/157

FOREIGN PATENT DOCUMENTS 0295656 12/1988 European Pat. Off. ............. 546/270
0356234 2/1990 European Pat. Off. ............. 546/270

OTHER PUBLICATIONS

Ulrich et al, Journal of Medicinal Chemistry, vol. 25, No. 6, pp. 654–657, 1982.
Lau et al., Journal of Organic Chemistry, vol. 35, No. 12, pp. 4103–4108, 1970.

Primary Examiner—C. Warren Ivy
Assistant Examiner—Zinna N. Davis
Attorney, Agent, or Firm—Birch, Stewart, Kolasch & Birch

[57] ABSTRACT

A benzothiazole derivative or a pharmacologically acceptable salt thereof which is useful as a preventive or therapeutic agent for diseases on which functions of suppressing leukotrienes and thromboxanes production are effective.

A benzothiazole derivative represented by the following general formula (I):

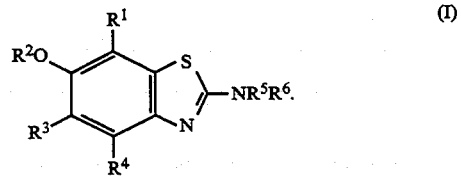

18 Claims, No Drawings

PYRIDYL SUBSTITUTED BENZOTHIAZOLE COMPOUNDS WHICH HAVE USEFUL PHARMACEUTICAL UTILITY

This application is a divisional of application Ser. No 07/861,379, filed on Mar. 31, 1992, U.S. Pat. No. 5,300,518, the entire contents of which are hereby incorporated by reference.

FIELD OF THE INVENTION

This invention relates to a benzothiazole derivative which is highly effective as a medicine. More particularly, it relates to a benzothiazole derivative useful as a preventive and therapeutic agent for diseases which functions to suppress the production of leukotrienes and thromboxanes.

DESCRIPTION OF THE RELATED ART

In recent years, a number of studies on leukotrienes and thromboxanes have been done. As it has been found out that these substances relate to various inflammatory diseases, attempts have been actively made to develop medicines capable of inhibiting thromboxane synthetase or 5-lipoxygenase.

Steroidal Antiinflammatory drugs such as prednisolone and nonsteroidal antiinflammatory drugs such as indomethacin and aspirin. Are currently widely used. However serious side effects of these steroidal drugs make them unsuitable for prolonged administration. On the other hand, nonsteroidal drugs (for example, indomethacin and aspirin) do not suppress the production of leukotrienes causing tissue damage but the production of prostaglandin E$_2$ which is believed to protect mucosa. Thus attention should be fully paid to the administration of these drugs.

It has been urgently required, therefore, to develop a medicine which suppresses the production of leukotrienes and thromboxanes which mediate inflammation but does not positively suppress the production of prostaglandin E$_2$ which protects mucosa.

SUMMARY OF THE INVENTION

Accordingly, it is an object of the present invention to provide a novel benzothiazole derivative useful for preventing and treating diseases on which leukotriene production inhibition, via the 5-lipoxygenase inhibition function and thromboxane production inhibition function, via the inhibition of thromboxane synthetase, are effective, and a pharmacologically acceptable salt thereof. Further, it is another object of the present invention to provide a method for producing the above-mentioned compound or a pharmacologically acceptable salt thereof. Furthermore, it is another object of the present invention to provide a medicine which comprises the above-mentioned compound or a pharmacologically acceptable salt thereof as an active ingredient.

Under these circumstances, the present inventors began to search for a novel medicine. As a result, they have successfully found that the above-mentioned objects can be achieved by using a benzothiazole derivative as will be described hereinbelow, thus completing the present invention.

The compound of the present invention is a benzothiazole derivative represented by the following general formula (I) and a pharmacologically acceptable salt thereof:

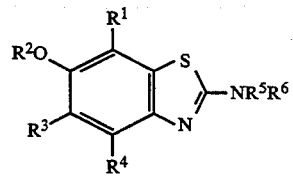

wherein R$^1$ and R$^3$ are either same or different and each represents a hydrogen atom, a lower alkyl group, a lower alkoxy group, a group represented by the formula:

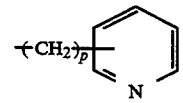

(wherein p is an integer of from 1 to 4), or a group represented by the formula:

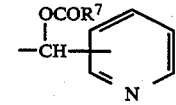

(wherein R$^7$ represents a lower alkyl group);
R$^4$ represents a hydrogen atom, a lower alkyl group, a phenyl group, a group represented by the formula:

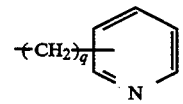

(wherein q is an integer of from 1 to 4), or a group represented by the formula:

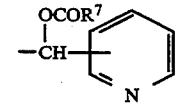

(wherein R$^7$ represents a lower alkyl group);
or R$^3$ and R$^4$ may form a benzene ring together with the carbon atoms to which they are bound;
R$^2$ represents a hydrogen atom or a protective group of a hydroxyl group; and
R$^5$ and R$^6$ are either same or different and each represents a hydrogen atom, a lower alkyl group, a group represented by the formula:

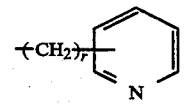

(wherein r is an integer of from 1 to 4), or an acyl group.

The benzothiazole derivative or a pharmacologically acceptable salt thereof includes the below listed benzothiazole derivatives and their pharmacologically acceptable salts:

6-Hydroxy-5,7-dimethyl-2-(3-pyridylmethyl)aminobenzothiazole

6-Hydroxy-4,5,7-trimethyl-2-(3-pyridylmethyl)aminobenzothiazole

6-Hydroxy-4,7-dimethyl-2-(3-pyridylmethyl)aminobenzothiazole

2-Ethylamino-6-hydroxy-4,7-dimethyl-5-(3-pyridylmethyl)benzothiazole

6-Hydroxy-5,7-dimethyl-2-methylamino-4-(3-pyridylmethyl)benzothiazole

2-Ethylamino-6-hydroxy-4,5-dimethyl-7-(3-pyridylmethyl)benzothiazole.

Further, the present invention provides a 5-lipoxygenase inhibitor, a thromboxane synthetase inhibitor, leukotrienes synthesis inhibitor and thromboxanes synthesis inhibitor each of which comprises the above-described benzothiazole derivative or a pharmacologically acceptable salt thereof as an active ingredient.

Furthermore, the present invention provides a preventive and therapeutic agent for diseases for which 5-lipoxygenase inhibition function is effective, thromboxane synthetase inhibition function is effective, leukotriene synthesis inhibition function is effective or thromboxane synthesis inhibition function is effective, and for inflammatory bowel diseases which comprises the above-described benzothiazole derivative or a pharmacologically acceptable salt thereof as an active ingredient.

The present invention provides a pharmacological composition which comprises a therapeutically effective amount of the above-described benzothiazole derivative or a pharmacologically acceptable salt thereof and a pharmacologically acceptable vehicle.

Further, the present invention provides use of the above-described benzothiazole derivative or a pharmacologically acceptable salt thereof for the making of a medicament for treating a disease which the activity of the 5-lipoxygenase is raised, the activity of thromboxane synthetase is raised, the synthesis of leukotrienes is raised or the synthesis of thromboxanes is raised and for the making of a medicament for treating inflammatory bowel diseases.

Furthermore, the present invention provides a method for treating a disease which comprises administering a pharmaceutically effective amount of the above-described benzothiazole derivative or a pharmacologically acceptable salt thereof to a patient suffering from a disease which the activity of the 5-lipoxygenase is raised, the activity of thromboxane synthetase is raised, the synthesis of leukotrienes is raised or the synthesis of thromboxanes is raised, or to a patient suffering from inflammatory bowel diseases.

DETAILED DESCRIPTION OF THE INVENTION

In the above description of the compound (I) of the present invention, the term "a lower alkyl group" given in the definition of $R^1$, $R^3$, $R^4$, $R^5$, $R^6$ and $R^7$ means a straight-chain or branched alkyl group having 1 to 6 carbon atoms, for example, methyl, ethyl, n-propyl, isopropyl, n-butyl, isobutyl, sec-butyl, tert-butyl, n-pentyl (amyl), isopentyl (isoamyl), neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, preferable examples include methyl, ethyl, n-propyl and isopropyl groups and a methyl group is particularly preferable.

The term "a lower alkoxy group" given in the definition of $R^1$ and $R^3$ means a straight-chain or branched alkoxy group having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, 1-methylbutoxy, 2-methylbutoxy, 1,2-dimethylpropoxy, and hexyloxy groups. Among these groups, preferable examples include methoxy and ethoxy groups and a methoxy group is particularly preferable.

The term "an acyl group" given in the definition of $R^5$ and $R^6$ may be any of aliphatic, aromatic and heterocyclic acyl groups, without restriction. Among these acyl groups, preferable examples include lower alkanoyl groups such as formyl, acetyl, propionyl, butyryl, valeryl, isovaleryl and pivaloyl groups, aroyl groups such as benzoyl, toluoyl and naphthoyl groups and heteroaryl groups such as furoyl, nicotinoyl and isonitocinoyl groups.

The substituent —$(CH_2)_p$— given in the group of the formula

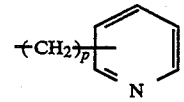

in the definition of $R^1$ and $R^3$ is preferably one located at the 3- or 4-position and p is preferably 1 or 2. It is particularly preferable that said substituent is one located at the 3-position and p is 1.

The substituent —$(CH_2)_q$— given in the group of the formula

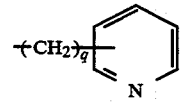

in the definition of $R^4$ is preferably one located at the 3- or 4-position and q is preferably 1 or 2. It is particularly preferable that said substituent is one located at the 3-position and q is 1.

The substituent —$(CH_2)_r$— given in the group of the formula

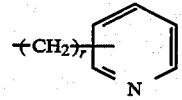

in the definition of $R^5$ and $R^6$ is preferably one located at the 3- or 4-position and r is preferably 1 or 2. It is particularly preferable that said substituent is one located at the 3-position and r is 1.

Examples of the protective group of a hydroxyl group given in the definition of $R^2$ include lower alkyl groups such as methyl and ethyl groups and acyl groups such as acetyl, propionyl, butyroyl, pivaloyl, nicotinoyl and benzoyl groups. Any protective group may be used therefor so long as it can be decomposed and thus liberated from the hydroxyl group by some means in vivo.

Examples of the pharmacologically acceptable salt to be used in the present invention include inorganic acid salts such as hydrochloride, hydrobromide, sulfate and phosphate, organic acid salts such as acetate, maleate, tartrate, methanesulfonate, benzenesulfonate and toluenesulfonate and amino acid salts such as arginate, aspartate and glutamate.

Furthermore, some compounds form salts with metals such as sodium, potassium, calcium and magnesium. These metals salts are also involved in the pharmacologically acceptable salt to be used in the present invention.

To further illustrate the present invention in greater detail, particularly preferable examples of the compounds of the present invention will be given. It is to be noted, however, that the present invention is not restricted thereto.

Examples of the most desirable compounds are those represented by the following general formula (A) and pharmacologically acceptable salts thereof.

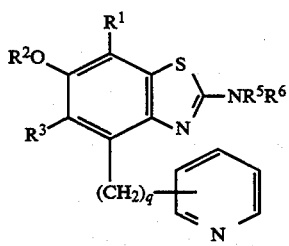
(A)

In the above formula, $R^1$, $R^2$, $R^3$, $R^5$, $R^6$ and q are as defined above.

$R^1$ and $R^3$ may be either same or different and preferably each represents a hydrogen atom, a lower alkyl group or a lower alkoxy group, still preferably a methyl group, an ethyl group, a methoxy group or an ethoxy group.

$R^2$ preferably represents a hydrogen atom, a methyl group or an acetyl group and a hydrogen atom is most desirable therefor.

In the group represented by the formula:

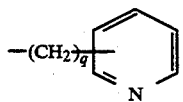

the straight-chain moiety is preferably located at the 4- or 3-position of the pyridine ring and q is preferably an integer of 1 or 2. Namely, groups represented by the formulae:

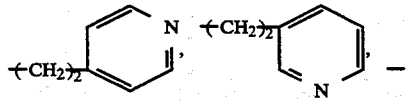

and

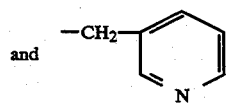

are preferable. Among these groups, the one represented by the formula:

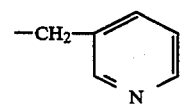

is most desirable.

$R^5$ and $R^6$ may be either same or different and preferably each represents a hydrogen atom or a lower alkyl group. A hydrogen atom, a methyl group, an ethyl group and a propyl group are preferable therefor. It is still preferable that either one of them is a hydrogen atom.

Examples of the next most desirable compounds are those represented by the following general formula (B) and pharmacologically acceptable salts thereof.

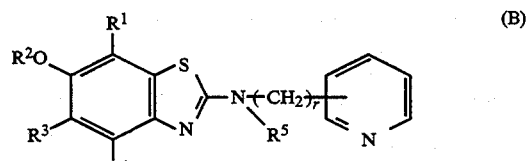
(B)

In the above formula, $R^1$, $R^2$, $R^3$, $R^4$, $R^5$ and r are as defined above.

$R^1$ and $R^3$ may be either same or different and preferably each represents a hydrogen atom, a lower alkyl group or a lower alkoxy group, still preferably a hydrogen atom, a methyl group, an ethyl group, a methoxy group or an ethoxy group.

$R^2$ preferably represents a hydrogen atom, a methyl group or an acetyl group and a hydrogen atom is most desirable therefor.

$R^4$ preferably represents a lower alkyl group and a methyl group and an ethyl group are most desirable therefor.

$R^5$ preferably represents a hydrogen atom or a lower alkyl group and a hydrogen atom is most desirable therefor.

In the group represented by the formula:

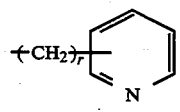

the straight-chain moiety is preferably located at the 4- or 3-position of the pyridine ring and r is preferably an integer of 1 or 2. Namely, groups represented by the formulae:

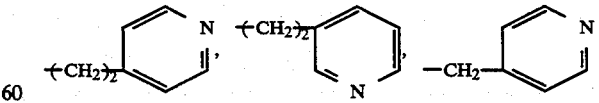

and

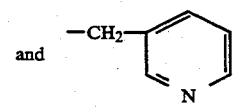

are preferable. Among these groups, the one represented by the formula:

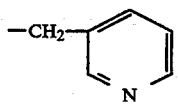

is most desirable.

Examples of the third most desirable compounds are those represented by the following general formula (C) and pharmacologically acceptable salts thereof.

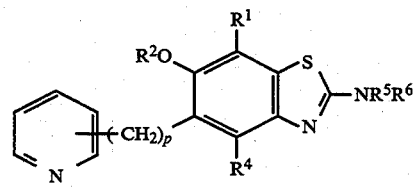

In the above formula, $R^1$, $R^2$, $R^4$, $R^5$, $R^6$ and p are as defined above.

$R^1$ preferably represents a hydrogen atom, a lower alkyl group or a lower alkoxy group, still preferably a methyl group, an ethyl group, a methoxy group or an ethoxy group.

$R^2$ preferably represents a hydrogen atom, a methyl group or an acetyl group and a hydrogen atom is most desirable therefor.

In the group represented by the formula:

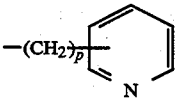

the straight-chain moiety is preferably located at the 4- or 3-position of the pyridine ring and p is preferably an integer of 1 or 2. Namely, groups represented by the formulae:

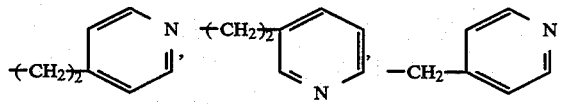

and

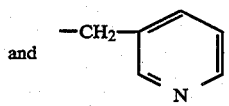

are preferable. Among these groups, the one represented by the formula:

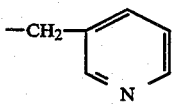

is most desirable.

$R^4$ preferably represents a lower alkyl group and a methyl group and an ethyl group are most desirable therefor.

$R^5$ and $R^6$ may be either same or different and each preferably represents a hydrogen atom or a lower alkyl group. A hydrogen atom, a methyl group, an ethyl group and a propyl group are preferable therefor. It is still preferable that either one of them is a hydrogen atom.

Production method

The compounds of the present invention can be produced by various methods. Typical examples of these methods will be now described.

Production method 1

When both of $R^5$ and $R^6$ in the general formula (I) are hydrogen atoms, the compound of the present invention may be produced by, for example, the following method.

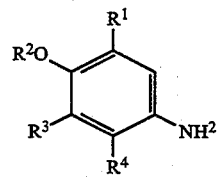

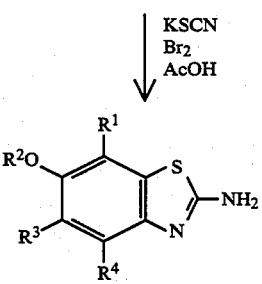

Namely, a compound represented by the general formula (II) is cyclized in the conventional manner to thereby give a compound represented by the general formula (III) which is one of the target compounds.

In this reaction, the compound (II) having an amino group is cyclized with the use of potassium thiocyanate and bromine. The reaction can be performed in accordance with, for example, the method described in Bellstein, 27 (2), 334. A mixture of acetic acid and water (1:1 to 95:5) may be cited as an example of the reaction solvent. The reaction temperature ranges from 0° C. to room temperature.

Production method 2

When the target compound of the general formula (I) is represented by the following formula (IV):

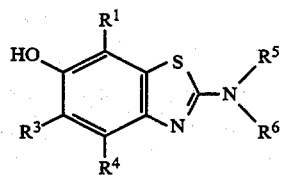

the target compound may be produced by the cyclizing method as will be given below:

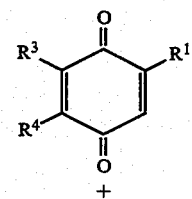

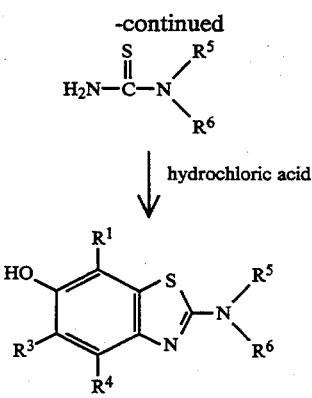

wherein $R^1$, $R^3$, $R^4$, $R^5$ and $R^6$ are as defined above.

In this reaction, 1,4-benzoquinone (V) is condensed with a thiourea derivative (VI) in the presence of concentrated hydrochloric acid in accordance with the method described in J. Org. Chem., 35, 4103 (1970) to thereby give the compound (IV).

Methanol or ethanol is usable as the solvent in this reaction. The reaction temperature ranges from 0° C. to the refluxing temperature of the selected solvent.

Production method 3 (via iminobromide)

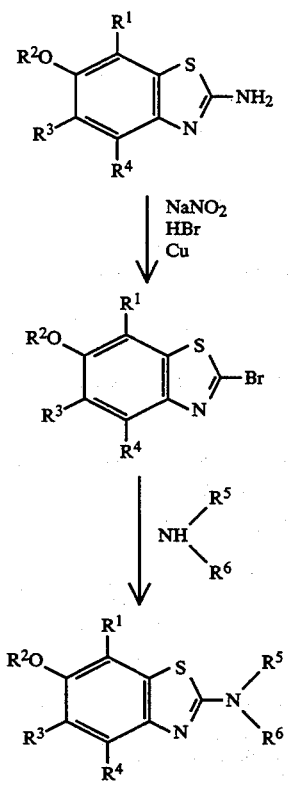

wherein $R^1$, $R^2$, $R^3$, $R^4$, $R^5$ and $R^6$ are as defined above.

In this reaction, the compound (VII) having an amino group is diazotized and the diazonium salt thus formed is decomposed to thereby give an iminobromide compound (VIII), in accordance with the method described in Organic Synthesis, Collective Volume 1, page 135. Sodium nitrite and hydrobromic acid are used as the diazotizing agent, while hydrobromic acid and copper are used for decomposing the diazonium salt. Any solvent may be used here so long as it does not take part in the reaction, and also hydrobromic acid is usable therefor. The reaction temperature ranges from 0° C. to the refluxing temperature of the solvent.

The iminobromide (VIII) is reacted with an amine (IX) in the presence of a base and thus the compound (X) is obtained. Any base may be used here and any solvent may be used so long as it does not take part in the reaction. Alternately, the reaction may be effected without using any solvent. The reaction temperature ranges from room temperature to 180° C.

Production method 4

When the target compound of the general formula (I) is one represented by the following formula (XI):

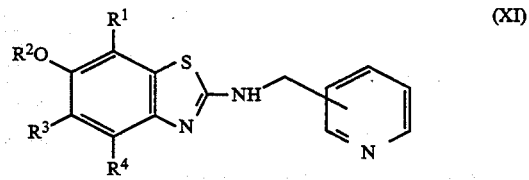

the target compound may be produced by the following method:

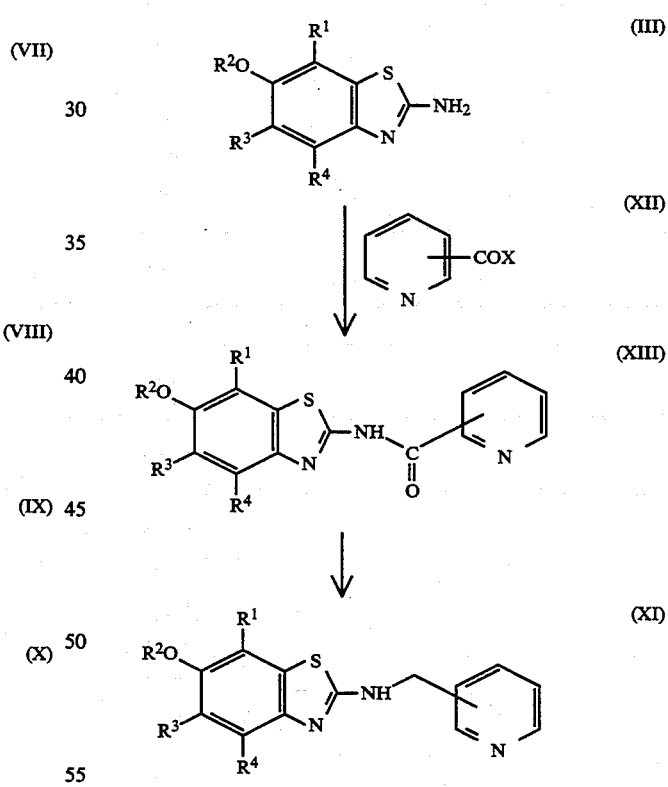

wherein $R^1$, $R^2$, $R^3$ and $R^4$ are as defined above; and X represents a halogen atom.

In this reaction, namely, the compound (III) having an amino group is reacted with an acid halide (XII), preferably in the presence of a base, to thereby give an amide compound (XIII). Next, the obtained amide compound (XIII) is reduced to thereby give the target compound (XI).

As the acid halide. an acid chloride or an acid bromide may be used. Examples of the base usable here include alkali metal carbonates or hydrogencarbonates such as sodium hydrogencarbonate, potassium carbonate and sodium carbonate, alkali hydroxides such as sodium hydroxide and potassium hydroxide, organic bases such as triethylamine, pyridine and diethylaniline, and sodium hydride. As an example of the reducing agent, diborane may be cited. Any solvent may be suitably selected here so long as it does not take part in the reaction. The reaction temperature usually ranges from 0° C. to the refluxing temperature of the solvent.

Production method 5

When the target compound of the general formula (I) is one represented by the following formula (XI):

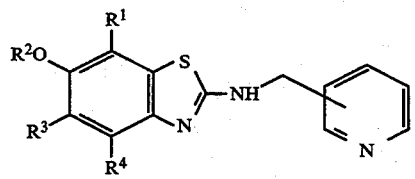
(XI)

the target compound may be produced by the following method via a Schiff base:

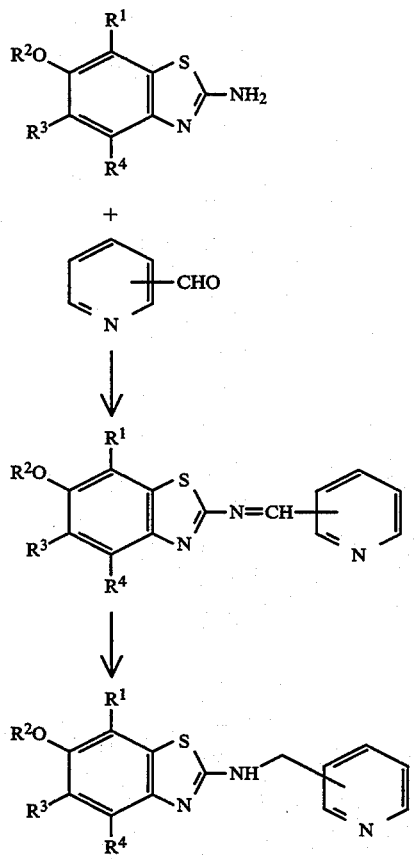

wherein $R^1$, $R^2$, $R^3$ and $R^4$ are as defined above.

The compound (III) having an amino group is reacted with an aldehyde (XIV), while removing the water thus formed, to thereby give a Schiff base (XV). In this stage, any solvent may be used so long as it does not take part in the reaction. Preferable examples of the solvent include benzene and toluene. The reaction temperature ranges from room temperature to the refluxing temperature of the solvent. The addition of a small amount of ammonium acetate serves to accelerate the reaction.

Next, the Schiff base (XV) thus obtained is reduced into an amine (XI). Examples of the reducing agent include lithium aluminum hydride, sodium borohydride and sodium borocyanohydride. Alternately, catalytic reduction may be effected with the use of palladium/carbon, platinum oxide or Raney nickel as the catalyst. Any solvent may be used in this reaction so long as it does not take part in the reaction. The reaction temperature ranges from 0° C. to the refluxing temperature of the selected solvent. Preferable examples of the solvent include tetrahydrofuran and diethyl ether when lithium aluminum hydride is used, methanol, ethanol and a mixture of water with an alcohol when sodium borohydride or sodium borocyanohydride is used, and ethyl acetate, methanol and ethanol when the catalytic reduction is effected.

Production method 6

When the target compound of the general formula (I) is one represented by the following formula (XVI):

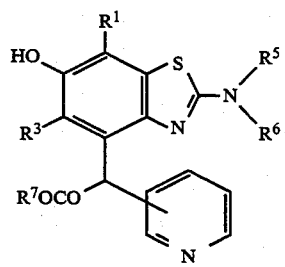
(XVI)

the target compound may be produced by the following method:

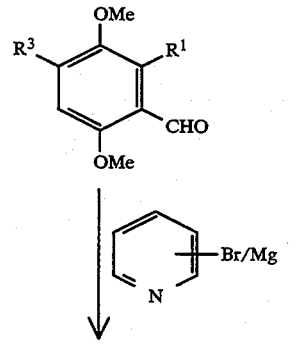

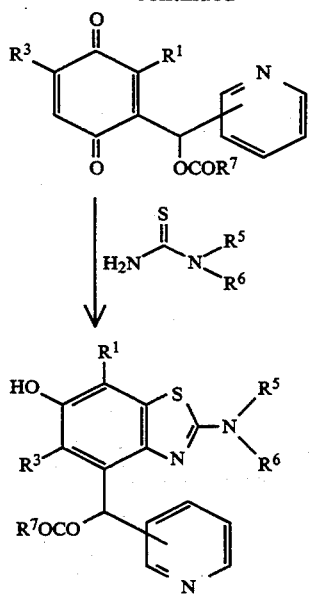

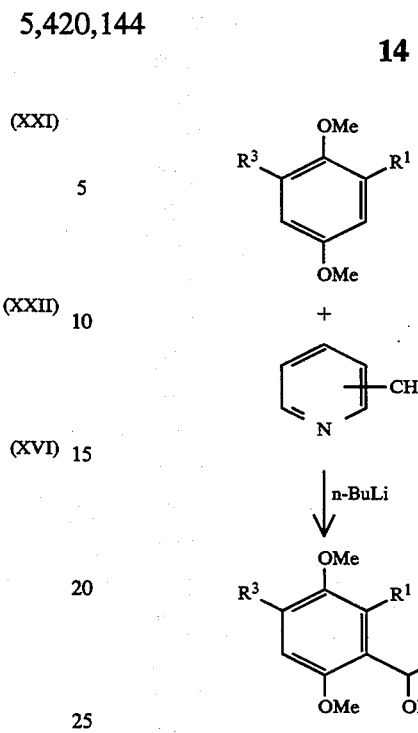

wherein $R^1$, $R^3$, $R^5$, $R^6$ and $R^7$ are as defined above; and Me represents a methyl group.

First, 2,5-dimethoxybenzaldehyde (XVII) and bromopyridine are subjected to the Grignard reaction in the presence of magnesium to thereby give a secondary alcohol (XVIII). Any solvent may be used here so long as it does not take part in the reaction. As a preferable example of the solvent, tetrahydrofuran may be cited. The reaction temperature ranges from 0° C. to the refluxing temperature of the solvent.

Next, the alcohol (XVIII) obtained above is reacted with an acid anhydride (XIX) to thereby give an acylated dimethyl ether (XX). Any solvent may be used here so long as it does not take part in the reaction. As a preferable example of the solvent, pyridine may be cited. The reaction temperature ranges from 0° C. to the refluxing temperature of the solvent.

Then the acylated dimethyl ether (XX) is oxidized into a quinone (XXI). As an example of the reaction solvent, acetonitrile/water may be cited. As an example of the oxidizing agent, ammonium ceric nitrate may be cited. The reaction temperature ranges from 0° C. to the refluxing temperature of the solvent.

The obtained quinone (XXI) is reacted with thiourea (XXII) in the presence of concentrated hydrochloric acid and thus the target compound (XVI) is obtained. Preferable examples of the solvent to be used here include methanol and ethanol.

In order to prepare the alcohol (XVIII) from 2,5-dimethoxybenzaldehyde (XVII), the aldehyde (XVII) is reacted with bromopyridine in the presence of n-butyllithium. In this reaction, any solvent may be used so long as it does not take part in the reaction. For example, tetrahydrofuran is usable therefor. The reaction temperature preferably ranges from −60° C. to −10° C.

Alternately, the alcohol (XVIII) may be obtained by the following method:

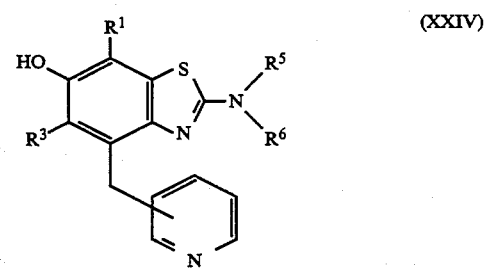

wherein $R^1$, $R^3$ and Me are as defined above.

In the presence of n-butyllithium, pyridylaldehyde (XIV) is reacted with dimethyl ether (XXIII) to thereby give the alcohol (XVIII). As the reaction solvent, for example, tetramethylethylenediamine/dry ether may be selected. The reaction temperature ranges from −65° C. to room temperature.

Production method 7 (deacylation)

When the target compound of the general formula (I) is one represented by the following formula (XXIV):

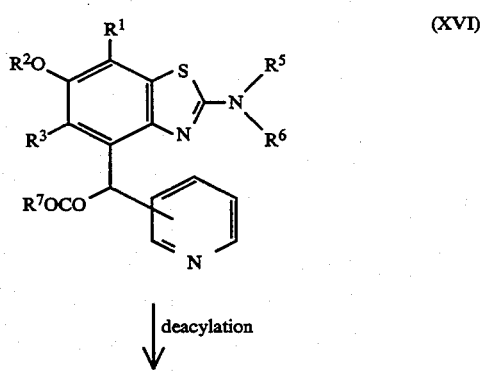

the target compound may be produced by the following method:

-continued

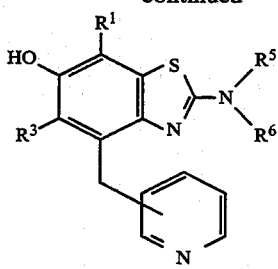
(XXIV)

wherein $R^1$, $R^2$, $R^3$, $R^5$, $R^6$ and $R^7$ are as defined above.

The acyl compound (XVI) is deacylated to thereby give a deacylated compound (XXIV). Examples of the deacylating agent include zinc/acetic acid and palladium/carbon. Any solvent may be used here so long as it does not take part in the reaction. The reaction temperature ranges from 0° C. to the refluxlng temperature of the solvent.

Production method 8 (demethylation)

When $R^2$ in the general formula (I) is a hydrogen atom, the target compound may be produced by the following method:

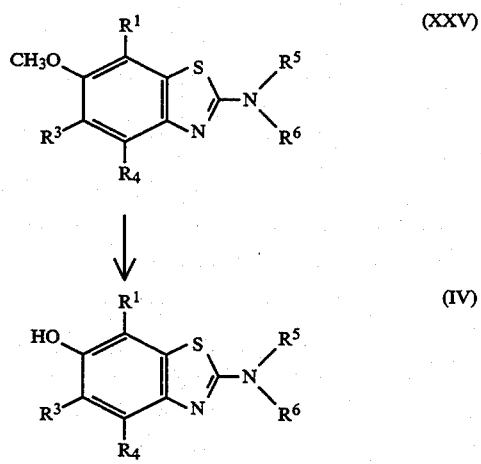

wherein $R^1$, $R^3$, $R^4$, $R^5$ and $R^6$ are as defined above.

The methyl compound (XXV) is demethylated to thereby give a demethylated compound (IV). Examples of the demethylating agent include boron tribromide, iodotrimethylsilane and hydrogen bromide/acetic acid. Any solvent may be used here so long as it does not take part in the reaction. Examples of the solvent include, in particular, methylene chloride and chloroform. The reaction temperature ranges from 0° C. to the refluxlng temperature of the solvent.

To illustrate the excellent effects of the compounds of the present invention in greater detail, the following Experimental Examples will be given.

Experimental Example 1

Function of suppressing production of leukotriene $B_4$ ($LTB_4$), thromboxane $B_2$ ($TxB_2$) and prostaglandin $E_2$ ($PGE_2$) from rat peritoneal exudation cells 10 ml of a 6% (w/v) solution of glycogen (Type II from Oyster, Sigma) in physiological saline was intraperitoneally injected into each of male Fisher rats weighing 150 to 200 g. After 20 to 24 hours, peritoneal exudation cells were collected from the rats, washed and suspended in the Hank's buffer salt solution (HBSS) at a concentration of $5 \times 10^6$/ml. Then 100 μl/well of the obtained cell suspension was piperred into a 96-well culture plate (Costar ®) containing 10 μl/well of a sample drug diluted to a given concentration. The plate was incubated at 37° C. for 5 minutes and A23187 (CALBIOCHEM ®) was added thereto so as to give a final concentration of 2 μg/ml. After incubating at 37° C. for additional 10 minutes, the plate was transferred on ice and a BW755C solution was added thereto so as to give a final concentration of 100 μM. This plate was centrifuged at 15,000 rpm for 10 minutes and the supernatant was collected. Then the $LTB_4$, $TxB_2$ and $PGE_2$ present in the supernatant were determined by enzyme immunoassay with the use of an EIA Kit manufactured by CAYMAN.

Table 1 shows the functions (expressed in $IC_{50}$) of each compound, represented by the compound number given in the Examples hereinbelow, of suppressing the production of $LTB_4$, $TxB_2$ and $PGE_2$.

TABLE 1

| Ex. No. | Production suppressing function $IC_{50}$ (μM) | | |
|---|---|---|---|
| | $LTB_4$ | $TxB_2$ | $PGE_2$ |
| 1 | 0.09 | 5.46 | enhanced at 1–10 μM, suppressed at 100 μM |
| 4 | <0.1 | 1.95 | enhanced at 0.1–1 μM, suppressed at 10 μM or above |
| 5 | <0.1 | 4.39 | enhanced at 0.1–10 μM, suppressed at 100 μM |
| 9 | 0.38 | 0.73 | enhanced at 0.1–100 μM |
| 10 | 0.10 | 0.09 | enhanced at 0.1–10 μM |
| 11 | <0.1 | 0.10 | enhanced at 0.1–10 μM, suppressed at 100 μM |
| 12 | <0.1 | 0.09 | enhanced at 0.1–10 μM, suppressed at 100 μM |
| 14 | 0.23 | 0.65 | enhanced at 0.1–1 μM, suppressed at 100 μM |
| 15 | 0.25 | 5.31 | enhanced at 0.1–100 μM |
| 17 | <0.1 | 2.00 | enhanced at 1 μM, suppressed at 100 μM |
| 18 | 0.19 | 0.002 | not determined |
| 20 | 0.17 | 0.11 | enhanced at 0.1–100 μM |
| 21 | 0.17 | 1.28 | not determined |
| 22 | 0.15 | 0.18 | not determined |
| 23 | <0.1 | 0.33 | enhanced at 0.1–10 μM, suppressed at 100 μM |

Experimental Example 2

Functions of suppressing production and liberation of $LTB_4$ and $TxB_2$ from TNB (trinitrobenzenesulfonic acid)colitis rat colon Rat TNB-colitis was induced in accordance with the method reported by Morris et al. [Gastroenterology, 96, 795–803 (1989)]. Namely, each of male F344 rats aged 9 weeks was fasted for 2 days and then etherized. A sound (1.2×80 mm, manufactured by Fuehigaml Kikai-ten) was inserted into the rectum of the animal to inject 0.25 ml of a 120 mg/ml solution of TNB (a product of Tokyo Kasei K. K.) in 50% ethanol into the colon cavity. The effects of each compound on the production and liberation of $LTB_4$ and $TxB_2$ from the colon of the TNB-colitis rat were evaluated by using the rat 7 days after the injection of TNB. Namely, each compound (5% suspension in methylcellulose) was orally administered to the rat in a dose of 0.5 ml/100 g body weight. After 6 hours, the animal was deeply etherized and subjected to autopsy. Thus the colon tissue was extirpated. The colon was incubated in Tyrode's solution (CALBIOCHEM containing 5 μg/ml of A23187-calcium ionophore) at 37° C. for 20 minutes in accordance with the method of Dreyling et al. [Biochim. Biophys. Acta, 878, 184-193 (1986)]. Then $LTB_4$, $TxB_2$ and $PGE_2$ thus produced and liberated into the medium were determined by radioimmunoassay (RIA). Next, the suppression ratios % were calculated based on the difference in the amounts of the produced and liberated $LTB_4$, $TxB_2$ and $PGE_2$ (ng/g of colon weight/20 min) between the control group, to which 5% methylcellulose alone was administered, and the test group.

Table 2 shows the results of typical compounds.

TABLE 2

| Ex. No. | Dose (mg/kg) | No. of animals | Suppression ratio (%) | | |
|---|---|---|---|---|---|
| | | | $LTB_4$ | $TxB_2$ | $PGE_2$ |
| 1 | 100 | 4 | 19 | 55 | 10 |
| 4 | 100 | 4 | 93 | 72 | 30 |
| 5 | 100 | 5 | 94 | 36 | 30 |
| 10 | 100 | 4 | 73 | 64 | 0 |
| 11 | 100 | 4 | 94 | 85 | 0 |
| 14 | 100 | 4 | 83 | 67 | 8 |
| 17 | 100 | 4 | 89 | 53 | 41 |

Experimental Example 3

Therapeutic effects on TNB-colitis

Rat TNB-colitis was induced in accordance with the method reported by Morris et al. [Gastroenterology, 96, 795-803 (1989)]. Namely, each of male F344 rats aged 9 weeks was fasted for 2 days and then etherized. A sound (1.2×80 mm, manufactured by Fuchigami Kikai-ten) was inserted into the rectum of the animal to inject 0.25 ml of a 120 mg/ml solution of TNB (a product of Tokyo Kasei K. K.) in 50% ethanol into the colon cavity. 3 days after the injection of TNB, each compound (5% suspension in methylcellulose) was orally administered once a day for 11 days. 14 days after the injection of TNB, the animal was subjected to autopsy and the colon was extirpated. The extent of damage to the colon was evaluated by determining MPO (myeloperoxidase) present therein.

The therapeutic ratio was calculated according to the following equation:

therapeutic ratio =
(5% methylcellulose group − ethanol group) −
(invention compound group − ethanol group).

Table 3 shows the results.

TABLE 3

| Ex. No. | Dose (mg/kg/day) | No. of animals | Therapeutic ratio (%) |
|---|---|---|---|
| 4 | 100 | 7 | 31 |
| 5 | 100 | 7 | 53 |
| 10 | 100 | 5 | 53 |
| 11 | 100 | 6 | 41 |
| 14 | 100 | 7 | 32 |
| 17 | 100 | 6 | 40 |
| prednisolone | 10 | 5 | 60 |

The above-mentioned results of the pharmacological experiments have revealed that the compound of the present invention suppresses the production of $LTB_4$ and $TxB_2$ and promote the production of $PGE_2$. Therefore the invention Compound is effective as a medicine capable of suppressing the production of leukotrienes and thromboxanes. The compound of the present invention is usable for preventing and treating diseases caused by leukotrienes, for example, skin diseases such as psoriasis and eczema, allergic rhinitis, asthma, cardiovascular diseases, hepatitis, nephritis, ulcerative coliris, temporal coliris, nonspecific coliris and Crohn's disease.

In addition, the present inventors have confirmed as the results of various experiments that the compound of the present invention suppresses the production of leukotrienes based on its patent activity of inhibiting 5-lipoxygenase and suppresses the production of thromboxanes based on its activity of inhibiting thromboxane synthetase.

Experimental Example 4

Toxicity test

6-Hydroxy-5,7-dimethyl-2-methylamino-4-(3-pyridylmethyl)benzothiazole obtained in Example 10 was administered to rats in a dose of 200 mg/kg once a day for 28 days repeatedly. However no abnormality caused by the administration of the drug was observed.

This result suggests that the compound of the present invention is highly safe and thus very useful from this viewpoint too.

When the compound of the present invention is to be administered as a preventive or therapeutic agent for these diseases, it may be formulated into tablets, granules, capsules, syrups or inhalations. The dose widely varies depending on the conditions, age and disease of the patient. In general, approximately from 0.1 to 1,000 mg/day, preferably from 1 to 500 mg/day, more preferably from 10 to 500 mg/day, of the compound may be administered to an adult one to several times per day.

The compound of the present invention may be formulated into preparations together with carriers commonly used in the art by the conventional methods. When a solid preparation for oral administration is to be produced, for example, the active component is mixed with fillers optionally together with binders, disintegrators, lubricants, colorants or corrigents and then formulated into, for example, tablets, coated tablets, granules, dusts or capsules in the conventional manner.

Examples of the fillers include lactose, corn starch, sucrose, glucose, sorbitol, crystalline cellulose and silicon dioxide. Examples of the binders include polyvinyl alcohol, polyvinyl ether, ethylcellulose, methylcellulose, gum arabic, tragacanth, gelatin, shellac, hydroxypropylcellulose, hydroxypropylmethylcellulose, calcium citrate, dextrin and pectin. Examples of the lubricants include magnesium stearate, talc, polyethylene glycol, silica and hardened vegetable oils. As the colorants, pharmaceutically authorized ones may be used. As the corrigents, cocoa powder, menthol, aromatic powder, mentha oil, borneol and powdered cinnamon bark may be used. Needless to say, these tablets and granules may be coated with sugar or gelatin, if desired.

When an injection is to be produced, the active component is optionally mixed with pH controllers, buffers, stabilizes or solubilizing agents and the obtained mixture is formulated into subcutaneous, intramuscular or intravenous injections by the conventional method.

EXAMPLES

To further illustrate the present invention, the following Examples will be given, though it is needless to say that the present invention is not restricted thereto.

Each Example will describe the final stage for producing the target compound of the present invention, while the starting materials to be used in the embodiment of these Examples will be dealt with in the Production Examples given before the Examples.

The symbols used in the chemical structural formulae respectively have the following meaning:
Me: a methyl group,
Et: an ethyl group,
Ac: an acetyl group, and
Ph: a phenyl group.

Production Example 1

α-(3-Pyridyl)-2,5-dimethoxy-4,6-dimethylbenzyl alcohol

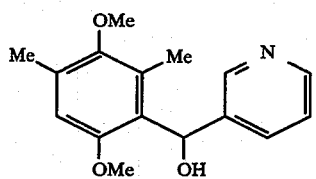

A four-necked flask containing 30 ml of dry tetrahydrofuran and 0.31 g of magnesium was heated to 60° C. in a nitrogen gas stream. After the heating was ceased, a small amount of iodine and then 0.18 g of dibromoethane were added to the flask. To the obtained suspension was added dropwise a solution of 0.50 g of bromopyridine and 1.78 g of dibromoethane in 5 ml of tetrahydrofuran while mildly refluxing the reaction mixture. After heating under reflux for 30 minutes, a solution of 0.61 g of 2,4-dimethyl-3,6-dimethoxybenzaldehyde in 3 ml of tetrahydrofuran was added dropwise thereto.

After the reaction mixture was cooled with ice, 30 ml of a saturated aqueous solution of ammonium chloride was added thereto and the mixture was extracted with ethyl acetate. The organic layer was washed with water and a saline solution and dried over magnesium sulfate. After distilling off the solvent, 0.72 g of a crude product of the title compound was obtained.

$^1$H-NMR(400 MHz,CDCl$_3$) δ (ppm): 2.28(s,3H), 2.31(s,3H), 3.65(s,3H), 3.68(s,3H), 4.30(d,1H,J=10.0 Hz), 6.05(d,1H,J=10.0 Hz), 6.61(s,1H), 7.21(dd,1H,J=4.5,7.5 Hz), 7.61(br.d,1H,J=7.5 Hz), 8.43(dd,1H,J=1.5,5.0 Hz), 8.48 (br.s,1H).

Production Example 2

α-(3-Pyridyl)-2,5-dimethoxy-4,6-dimethylbenzyl alcohol

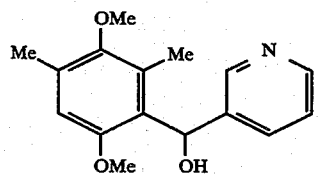

A four-necked flask containing 100 ml of dry ether was cooled to −50° C. in a nitrogen gas stream.

Then 48 ml of a 1.6M solution of n-butyllithium in hexane was added thereto. After cooling to −60° C., 7.4 ml of 3-bromopyridine was added thereto in portions. Then the mixture was stirred at −60° C. for 30 minutes and a solution of 9.9 g of 2,4-dimethyl-3,6-dimethoxybenzaldehyde in 100 ml of dry ether and 40 ml of dry tetrahydrofuran was added dropwise thereto. After the completion of the addition, the cooling bath was taken off. When the temperature of the reaction mixture reached −10° C., water was added thereto and the mixture was extracted with ethyl acetate. After washing with a saline solution and drying, the solvent was distilled off. Then the residue was purified by silica gel column chromatography (ethyl acetate:hexane=1-:5–5:1). Thus 14.0 g of the title compound was obtained.

Production Example 3

α-(3-Pyridyl)-2,5-dimethoxy-4,6-dimethylbenzyl alcohol

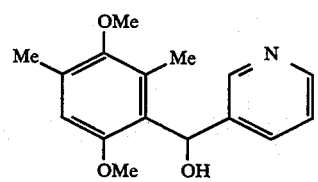

3.0 g of 1,3-dimethyl-2,5-dimethoxybenzene and 3.1 g of tetramethylethylenediamine were dissolved in 30 ml of dry ether and 17 ml of a 1.6M solution of n-butyllithium in hexane was added dropwise thereto in a nitrogen atmosphere at room temperature. After 1 hour, the mixture was cooled to −65° C. and a solution of 2.9 g of nicotinaldehyde in 10 ml of ether was added thereto. After 30 minutes, the reaction was ceased by adding water and the reaction mixture was extracted with ethyl acetate. The organic layer was dried over magnesium sulfate. After distilling off the solvent, 6.4 g of a crude product of the title compound was obtained.

Production Example 4

α-(3-Pyridyl)-2,5-dimethoxy-4,6-dimethylbenzyl acetate

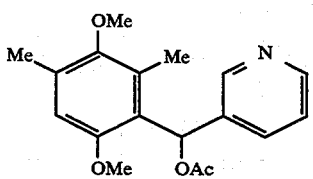

A mixture comprising 3.2 g of α-(3-pyridyl)-2,5-dimethoxy-4,6-dimethylbenzyl alcohol obtained by the method described in any of the Production Examples 1, 2 and 3, 5 ml of pyridine and 5 ml of acetic anhydride was heated and stirred at 80° C. for 1 hour. Then the pyridine and acetic anhydride were distilled off and the residue was purified by silica gel column chromatography. Thus 2.9 g of the title compound was obtained.

$^1$H-NMR(400 MHz,CDCl$_3$) δ (ppm): 2.17(s,6H), 2.28(s,3H), 3.61(s,3H), 3.75(s,3H), 6.61(s,1H), 7.22(dd,1H,J=4.5,7.5 Hz), 7.50(dt.1H,J=1.5,7.5 Hz), 7.59(s,1H), 8.45(br.s,2H).

Production Example 5

{2-(3,5-Dimethyl-1,4-benzoquinonyl)}-(3-pyridyl)-methyl acetate

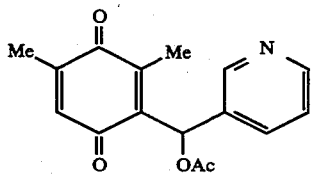

3.5 g of α-(3-pyridyl)-2,5-dimethoxy-4,6-dimethylbenzyl acetate obtained in the Production Example 4 was dissolved in a solvent mixture comprising 35 ml of acetonitrile and 17 ml of water. Then 12.2 g of ammonium ceric nitrate was added thereto in portions. After stirring at room temperature for 1 hour, the mixture was neutralized with a saturated aqueous solution of sodium hydrogencarbonate. 100 ml of ethyl acetate was added thereto and the mixture was filtered with Celite. The aqueous layer was further extracted with ethyl acetate. The organic layers were combined, washed with a saline solution and dried over magnesium sulfate. After distilling off the solvent, 3.1 g of the title compound was obtained as a yellow oily product.

$^1$H-NMR(400 MHz,CDCl$_3$) δ (ppm): 2.07(s,3H), 2.13(s,3H), 2.20(s,3H), 6.61(s,1H), 7.14(s,1H), 7.28(dd,1H,J=4.5,7.5 Hz), 7.66(dt.1H,J=1.5,7.5 Hz), 8.45(dt,1H,J=1.5,4.5 Hz), 8.59(br.s,1H).

Production Example 6

2-Amino-6-hydroxy-4,7-dimethylbenzothiazole hydrochloride

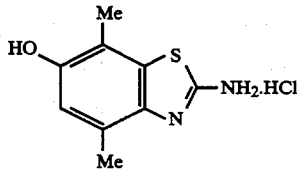

To 2.24 g of thiourea were added 60 ml of ethanol and 2.5 ml of concentrated hydrochloric acid, followed by stirring. Then a solution of 8.0 g of p-xyloquinone in ethanol (120 ml) was slowly added dropwise thereto. The reaction mixture was stirred at room temperature for 24 hours and then concentrated to about one-half. The crystals thus precipitated were separated by filtering and washed with a small amount of ethanol. Thus 6.80 g of the title compound was obtained in the form of white crystals.

$^1$H-NMR(400 MHz,d$_6$-DMSO) δ (ppm): 2.14(s,3H), 2.34(s,3H), 3.71(br.s,3H), 6.73(s,1H).

Production Example 7

2-Amino-6-methoxy-4,5,7-trimethylbenzothiazole

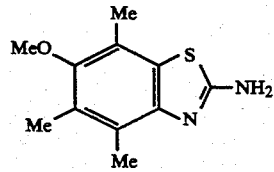

100 g of 1-amino-4-methoxy-2,3,5-trimethylbenzene was dissolved in 1,000 ml of acetic acid and 50 ml of water. Then 212 g of potassium thiocyanate was added to the solution at room temperature. The reaction mixture was cooled with ice and 37.5 ml of bromine was added dropwise thereto, followed by stirring for 30 minutes. The reaction mixture was neutralized with a 1N aqueous solution of sodium hydroxide. The insoluble matters thus formed were separated by filtering and washed with water. After recrystallizing from methanol/tetrahydrofuran, 123 g of the title compound was obtained.

$^1$H-NMR(400 MHz,d$_6$-DMSO.) δ (ppm): 2.16(s,3H), 2.24(s,3H), 2.35(s,3H), 3.59(s,3H).

Production Example 8

6-Methoxy-4,5,7-trimethyl-2-(3-pyridinecarboxamido)-benzothiazole

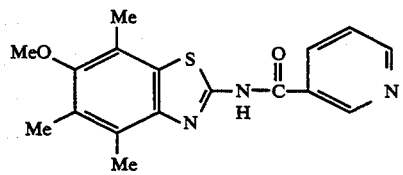

2.2 g of 2-amino-6-methoxy-4,5,7-trimethylbenzothiazole obtained in the above Production Example 7 and 2.7 g of nicotinic acid chloride hydrochloride were suspended in 50 ml of tetrahydrofuran and 3 ml of pyridine was added thereto at room temperature. After heating and stirring the mixture at 60° C. for 2 hours, the reaction was ceased by adding water. The crystals thus precipitated were separated by filtering, washed with water and dried. Thus 2.7 g of the title compound as obtained.

$^1$H-NMR(90MHz,CDCl$_3$) δ (ppm): 2.35(s,3H), 2.50(s,3H), 2.60(s,3H), 3.76(s,3H), 7.41(dd,J=7 Hz,5 Hz,1H), 8.32~8.52(m,1H), 8.74(d,J=5 Hz,1H), 9.32(s,1H).

Production Example 9

6-Benzyloxy-5,7-dimethoxy-2-(3-pyridylmethyl)aminobenzothiazole

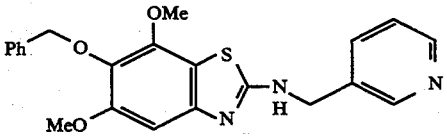

A mixture of 0.38 g of 6-benzyloxy-2-bromo-5,7-dimethoxybenzothiazole and 0.32 g of 3-aminomethylpyridine was heated and stirred at 120° C. for 4 hours. After adding water, the mixture was extracted with ethyl acetate and the organic layer was dried over magnesium sulfate. After distilling off the solvent, the obtained crude product was crystallized from ether. Thus 0.36 g of the title compound was obtained.

$^1$H-NMR(400 MHz,CDCl$_3$) δ (ppm): 3.86(s,3H), 3.96(s,3H), 4.68(s,2H), 5.01(s,2H), 5.47(br.s,1H), 6.94(s,1H), 7.26~7.40(m,4H), 7.49(d,J=7.0 Hz,2H), 7.76(d,J=7.5 Hz,1H), 8.56(dd,J=1.7,4.8 Hz,1H), 8.66(d,J=1.7 Hz,1H).

EXAMPLE 1

6-hydroxy-5,7-dimethoxy-2-(3-pyridylmethyl-)aminobenzothiazole

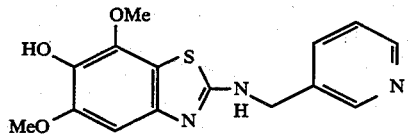

A mixture comprising 0.36 μg of 6-benzyloxy-5,7-dimethoxy-2-(3-pyridylmethyl)aminobenzothiazole obtained in the above Production Example 9, 10 ml of ethanol and 5 ml of concentrated hydrochloric acid was heated under reflux for 2 hours. Then the mixture was neutralized with a saturated aqueous solution of sodium hydrogencarbonate and extracted with ethyl acetate. The organic layer was dried over magnesium sulfate. After distilling off the solvent, the obtained crude product was crystallized from ethyl acetate. Thus 0.18 g of the title compound was obtained.

$^1$H-NMR(400 MHz,d6-DMSO) δ (ppm): 3.77(s,3H), 3.81(s,3H), 4.56(d,J=5.5 Hz, 2H), 6.86(s,1H), 7.37(dd,J=4.8,7.5 Hz,1H), 7.77(d,J=7.5 Hz,1H), 8.31(t,J=5.5 Hz,1H), 8.36(s,1H), 8.47(dd,J=1.7,4.8 Hz,1H), 8.59(d,J=1.7 Hz,1H).

EXAMPLE 2

6-Methoxy-4,5,7-trimethyl-2-(3-pyridylmethyl-)aminobenzothiazole

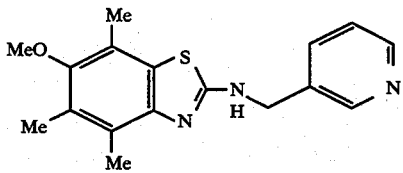

0.3 g of 6-methoxy-4,5,7-trimethyl-2-(3-pyridinecarboxamido)benzothiazole obtained in the above Production Example 8 was suspended in 30 ml of tetrahydrofuran. Then 10 ml of a 1.0M solution of borane/THF complex in tetrahydrofuran was added thereto and the mixture was heated under reflux for 30 minutes. After adding 20 ml of 1N hydrochloric acid, the mixture was further heated and stirred at 60° C. for 15 minutes. Then the mixture was neutralized with a saturated aqueous solution of sodium hydrogencarbonate and extracted with ethyl acetate. The organic layer was dried over magnesium sulfate. After distilling off the solvent, 0.3 g of the title compound was obtained.

$^1$H-NMR(400 MHz,CDCl$_3$) δ (ppm): 2.27(s,3H), 2.33(s,3H), 2.48(s,3H), 3.68(s,3H), 4.65(s,2H), 5.40(brs,1H), 7.29(dd,J=4.8,7.5 Hz, 1H), 7.77(d,J=7.5 Hz,1H), 8.55(dd,J=1.7,4.8 Hz,1H), 8.67(d.J=1.7 Hz,1H).

EXAMPLE 3

6-Methoxy-4,5,7-trimethyl-2-(3-pyridylmethyl-)aminobenzothiazole

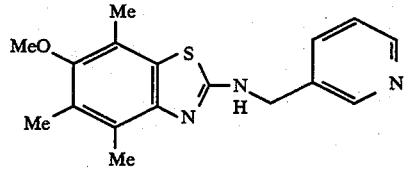

From 17.1 g (0.06 mol) of 2-bromo-6-methoxy-4,5,7-trimethylbenzothiazole and 19.4 g of 3-aminomethylpyridine, 15.9 g of the title compound was obtained by the same method as the one described in the Production Example 9.

EXAMPLE 4

6-Hydroxy-4,5,7-trimethyl-2-(3-pyridylmethyl-)aminobenzothiazole

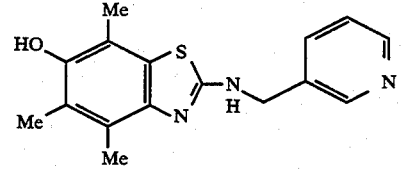

0.3 g of 6-methoxy-4,5,7-trimethyl-2-(3-pyridylmethyl)-aminobenzothiazole obtained in the above Example 2 or 3 was dissolved in 10 ml of dichloromethane and 5 ml of a 1.0M solution of boron tribromide in dichloromethane was added thereto. After stirring at room temperature for 30 minutes, the mixture was neutralized with a saturated aqueous solution of sodium hydrogencarbonate and extracted with ethyl acetate. The organic layer was dried over magnesium sulfate. After distilling off the solvent, the obtained crude product was crystallized from ethyl acetate. Thus 0.1 g of the title compound was obtained.

$^1$H-NMR(400 MHz,d$_6$-DMSO) δ (ppm): 2.12(s,3H), 2.18(s,3H), 2.35(s,3H), 4.55(d,J=5.7 Hz,2H), 7.36 (dd, J=4.8,7.5 Hz,1H ), 7.81(d,J=7.5 Hz,1H), 7.90(s,1H), 8.16(t,J=5.7 Hz,1H), 8.46(dd,J=1.7,4.8 Hz,1H), 8.62(d,J=1.7 Hz,1H).

EXAMPLE 5

6-Hydroxy-4,7-dimethyl-2-(3-pyridylmethyl)aminobenzothiazole

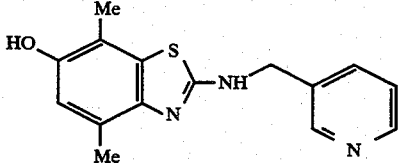

10.0 g of 2-amino-6-hydroxy-4,7-dimethylbenzothiazole hydrochloride obtained in the above Production Example 6 was suspended in 500 ml of toluene and 33.4 g of ammonium acetate was added thereto. Then the reaction mixture was vigorously stirred and heated under reflux for about 5 hours, while removing the formed water with a Dean-Stark extractor. After cooling in an ice bath, the orange crystals thus precipitated were separated by filtering. The crystals were washed with water and dried to thereby give 12.4 g of a crude imine. 10.7 g of this imine was suspended in 200 ml of ethanol and stirred in an ice bath. 1.33 g of sodium borohydride was added thereto in portions. The mixture was stirred at ice temperature for 3 hours and then neutralized by adding 10% hydrochloric acid thereto in portions. After extracting with ethyl acetate, the organic layer was washed with a saline solution and dried over magnesium sulfate. After distilling off the solvent, the residue was purified by silica gel column chromatography (solvent: ethyl acetate:hexane=1:3–4:1) to thereby obtain 5.2 g of the title compound as a pale yellow product.

$^1$H-NMR(400 MHz,d$_6$-DMSO) δ (ppm): 2.10(s,3H), 2.43(s,3H), 4.51(d,2H,J=6.0 Hz), 6.55(s,1H), 7.34(dd,1H,J=4,5,7.5 Hz), 7.78(br.d,1H,J=7.5 Hz), 8.17(t,1H,J=6 Hz), 8.43(d,1H,J=4.5 Hz), 8.57(s,1H), 8.90(s,1H).

Examples 6 to 8

The compounds as given below were obtained in accordance with the method described in the above Example 5.

EXAMPLE 6

6-Hydroxy-4-phenyl-2-(3-pyridylmethyl)aminobenzothiazole

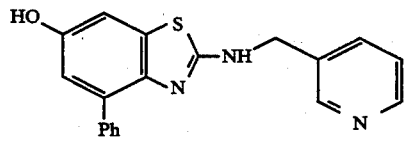

$^1$H-NMR(400 MHz,d$_6$-DMSO) δ (ppm): 4.49(d,1H,J=7.0 Hz), 7.00(s,1H), 7.30~7.46(m,5H), 7.64(s,1H), 7.66(s,1H), 7.76(br.d,1H,J=7 Hz), 8.47(d,1H,J=5 Hz), 8.54~8.60(m,2H).

EXAMPLE 7

6-Hydroxy-4,5,7-trimethyl-2-(4-pyridylmethyl)aminobenzothiazole

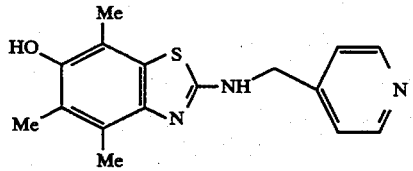

$^1$H-NMR(400 MHz ,CDCl$_3$) δ (ppm): 2.24(s,3H), 2.30(s,3H), 2.47(s,3H), 4.26(s,2H), 7.36(d,2H,J=6.0 Hz), 8.51(d,2H,J=6.0 Hz).

EXAMPLE 8

5-Hydroxy-4-methyl-2-(3-pyridylmethyl)aminonaphtho[1,2-d]thiazole

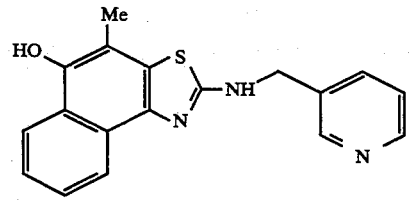

$^1$H-NMR (400 MHz, d$_6$-DMSO) δ (ppm): 2.41(s,3H), 4.68(d,1H,J=4.5 Hz), 7.38(dd,1H,J=4.5,7.5 Hz,), 7.39~7.48(m,2H), 7,87(br.d,1H,J=7.5 Hz), 8.18(d,1H,J=8 Hz), 8.31(d,1H,J=8 Hz), 8.42(dd,1H,J=1.5,4.5 Hz,), 8.47(d,1H,J=1.5 Hz), 8.71(s,1H), 8.32(br.s,1H).

EXAMPLE 9

{4-(6-Hydroxy-5,7-dimethyl-2-methylamino)benzothiazoyl}-(3-pyridyl)methyl acetate

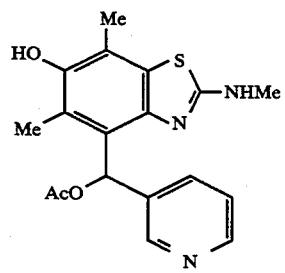

To 0.48 g of 1-methyl-2-thiourea were added 20 ml of ethanol and 1.4 ml of concentrated hydrochloric acid and stirred. Then a solution of 3.0 g of {2-(3,5-dimethyl-1,4-benzoquinonyl)}-(3-pyridyl)methyl acetate produced in the above Production Example 5 in ethanol (total volume: 12 ml) was added dropwise thereto within 30 minutes. After stirring at room temperature overnight, the crystals thus precipitated were separated by filtering, dissolved in 10 ml of water and neutralized with a saturated aqueous solution of sodium hydrogencarbonate. After extracting with ethyl acetate, the organic layer was washed with a saline solution and dried over magnesium sulfate. After distilling off the solvent, 1.0 g of the title compound was obtained as white crystals.

$^1$H-NMR(400 MHz,CDCl$_3$) δ (ppm): 2.17(s,3H), 2.20(s,1H), 2.35(s,3H), 3.05(s,3H), 7.20(dd,1H,J=4.5,7.5 Hz), 7.54(br.d,1H,J=7.5 Hz), 8.05(s,1 Hz), 8.45(d,1H,J=4.5 Hz), 8.52(d,1H,J=1.5 Hz).

EXAMPLE 10

6-Hydroxy-5,7-dimethyl-2-methylamino-4-(3-pyridyl-methyl)benzothiazole

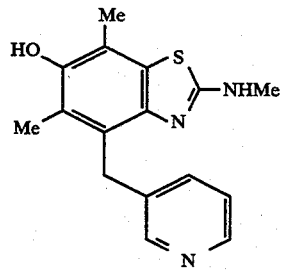

0.5 g of {4-(6-hydroxy-5,7-dimethyl-2-methylamino)-benzothiazoyl}-(3-pyridyl)methyl acetate obtained in the above Example 9 was dissolved in 5 ml of acetic acid. 0.75 g of zinc was added thereto and the mixture was heated under reflux for 5 hours. After adding water, the mixture was extracted with ethyl acetate and the organic layer was dried over magnesium sulfate. After distilling off the solvent, the obtained crude product was recrystallized from ethanol. Thus 0.26 g of the title compound was obtained.

m.p.: 236°~238° C. $^1$H-NMR(400 MHz,d$_6$-DMSO) δ (ppm): 2.10(s,3H), 2.23(s,3H), 2.90(d,3H,J=4.5 Hz), 4.27(s,2H), 7.22(dd,1H,J=4.5,7.5 Hz), 7.50(brd.d,1H,J=7.5 Hz,), 7.63(br.s,1H), 7.89~7.94(m,1H), 8.30(br.d,1H,J=5.0 Hz), 8.46(br.s,1H).

Examples 11 to 23

The following compounds were produced by the method similar to those described in the above Examples 9 and 10.

EXAMPLE 11

2-Ethylamino-6-hydroxy-5,7-dimethyl-4-(3-pyridylmethyl)benzothiazole dihydrochloride

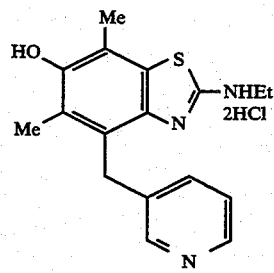

$^1$H-NMR(400 MHz,d$_6$-DMSO) δ (ppm): 1.23(t,3H,J=7.0 Hz), 2.14(s,3H), 2.28(s,3H), 3.51(dt,2H,J=7.0,5.0 Hz), 4.60(s,2H), 7.98(t,1H,J=7.0 Hz), 8.31(d,1H,J=7.0 Hz,), 8.75(s,1H), 8.78(d,1H,J=7.0 Hz).

EXAMPLE 12

6-Hydroxy-5,7-dimethyl-2-propylamino-4-(3-pyridyl-methyl)benzothiazole dihydrochloride

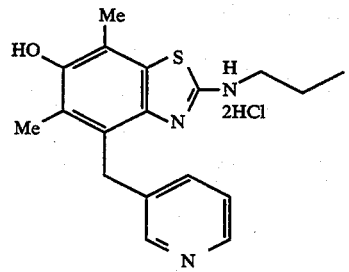

$^1$H-NMR(400 MHz, d$_6$-DMSO) δ (ppm): 0.90(t,3H,J=7.5 Hz), 1.58(q,2H,J=7.0 Hz), 2.10(s,3H), 2.24(s,3H), 3.40(br.s,2H), 4.56(s,2H), 7.94(dd,1H,J=5.5,8.0 Hz), 8.26(d,1H,J=8.0 Hz,), 8.72(s,1H), 8.74(d,1H,J=5.5 Hz).

EXAMPLE 13

6-Hydroxy-4,7-dimethyl-2-methylamino-5-(3-pyridyl-methyl)benzothiazole

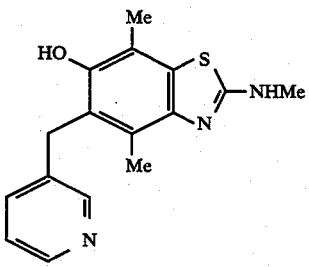

$^1$H-NMR(400 MHz,d$_6$-DMSO) δ (ppm): 2.13(s,3H), 2.29(s,3H), 2.90(d,3H,J=4.5 Hz), 4.25(s,2H), 7.95(dd,1H,J=8.0,4.5 Hz), 8.31(d,1H,J=8.0 Hz,), 8.68(s,1H), 8.75(d,1H,J=4.8 Hz,), 5.93(m,2H).

EXAMPLE 14

2-Ethylamino-6-hydroxy-4,7-dimethyl-5-(3-pyridylmethyl)benzothiazole

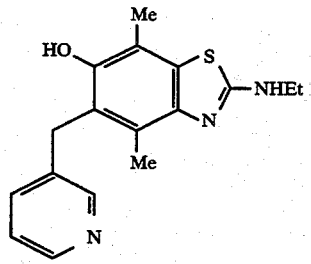

$^1$H-NMR(400 MHz,d$_6$-DMSO) δ (ppm): 1.18(t,3H,J=7.1 Hz), 2.24(s,3H), 2.34(s,3H), 3.34(m,2H), 4.06(s,2H), 7.23(dd,1H,J=7.8,4.5 Hz,), 7.44(d,1H,J=7.8 Hz,), 7.63(t,1H,J=5.1 Hz,), 8.15(br.s,1H), 8.33(dd,1H,J=4.8,1.5 Hz), 8.41(d,1H,J=2.2 Hz).

EXAMPLE 15

2-Amino-6-hydroxy-4,5-dimethyl-7-(3-pyridylmethyl)-benzothiazole dihydrochloride

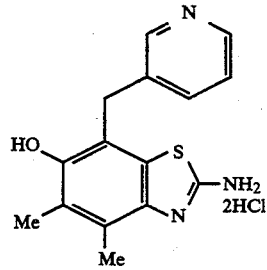

$^1$H-NMR(400 MHz,dG-DMSO) δ (ppm): 2.20(s,3H), 2.39(s,3H), 4.30(s,2H), 7.95(dd,1H,J=7.8,4.8 Hz,), 8.28(d,1H,J=7.5 Hz,), 8.75(s,1H), 8.78(d,1H,J=4.5 Hz).

EXAMPLE 16

6-Hydroxy-5,7-dimethyl-2-methylamino-4-(3-pyridyl-methyl)benzothiazole dihydrochloride

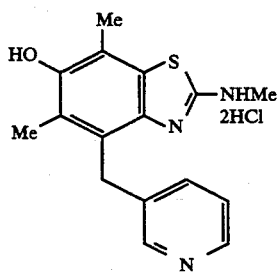

m.p.: 296°~298° C. $^1$H-NMR(400 MHz,d$_6$-DMSO) δ (ppm): 2.14(s,3H), 2.26(s,3H), 3.00(d,3H,J=0.5 Hz), 4.53(s,2H), 7.95(t,1H,J=7.0 Hz), 8.32(d,1H,J=7 Hz), 8.77(br.s,1H), 8.75(br.s,1H).

EXAMPLE 17

2-Ethylamino-6-hydroxy-4,5-dimethyl-7-(3-pyridylme-thyl)benzothiazole

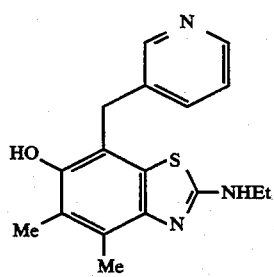

$^1$H-NMR(400 MHz,d$_6$-DMSO) δ (ppm): 1.13(t,3H,J=7 Hz), 2.14(s,3H), 2.35(s,3H), 3.30(m,2H), 3.98(s,2H), 7.23(dd,1H,J=7.8,4.5 Hz), 7.53(ddd,1H,J=7.8,4.8,2.4 Hz), 8.11(s,1H), 8.33(d,1H,J=4.5 Hz), 8.40(d,1H,J=2.4 Hz).

EXAMPLE 18

2-Amino-6-hydroxy-5,7-dimethyl-4-(3-pyridylmethyl)-benzothiazole dihydrochloride

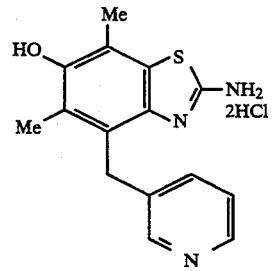

$^1$H-NMR(400 MHz ,d$_6$-DMSO) δ (ppm): 2.08(s,3H), 2.25(s,3H), 4.50(s,2H), 7.94(dd,1H,J=7.0,6.0 Hz), 8.20(d,1H,J=7.0 Hz), 8.71(s,1H), 8.75(d,1H,J=6.0 Hz).

EXAMPLE 19

6-Hydroxy-5,7-dimethoxy-2-methylamino-4-(3-pyridylmethyl) benzothiazole

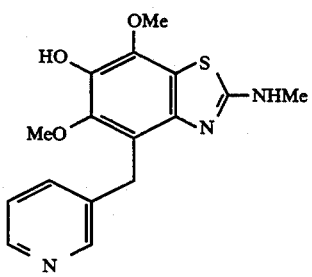

$^1$H-NMR(400 MHz,CDCl$_3$) δ (ppm): 3.07(s,3H), 3.78(s,3H), 3.97(s,3H), 4.26(s,2H), 7.13(dd,1H,J=8.0,4.5 Hz), 8.33(ddd,1H,J=8.0, 2.4,1.6 Hz), 8.37(dd,1H,J=4.8,1.6 Hz), 8.64(d,1H,J=2.4 Hz). Mass: FAB(Pos) m/z 322(M+H)+

EXAMPLE 20

2-Amino-6-hydroxy-5-methoxy-7-methyl-4-(3-pyridyl-methyl)benzothiazole dihydrochloride

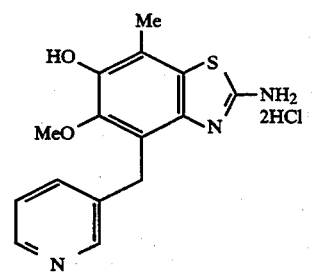

$^1$H-NMR(400 MHz,d$_6$-DMSO) δ (ppm): 2.21(s,3H), 3.65(s,3H), 4.40(s,2H), 7.17(s,1H), 7.30(s,1H), 7.43(s,1H), 7.94(dd,1H,J=8.0,5.6 Hz), 8.35(d,1H,J=8.0 Hz), 8.75(d,1H,J=5.6 Hz), 8.80(bs,1H).

EXAMPLE 21

6-Hydroxy-5-methoxy-7-methyl-2-methylamino-4-(3-pyridylmethyl)benzothiazole dihydrochloride

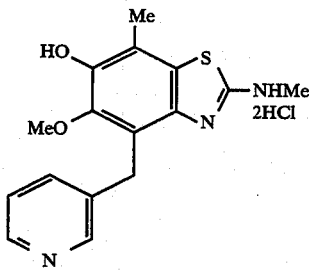

$^1$H-NMR(400 MHz, d$_6$-DMSO) δ (ppm): 2.18(s,3H), 2.94(s,3H), 3.66(s,3H), 4.39(s,2H), 7.94 (dd, 1H,J=8.0,5.6 Hz), 8.37(bd,1H,J=8.0 Hz), 8.73(d,1H,J=5.6 Hz), 8.81(bs,1H). Mass: FAB(Pos) m/z 316(M+H)+

EXAMPLE 22

2-Amino-7-ethyl-6-hydroxy-5-methoxy-4-(3-pyridylmethyl)benzothiazole dihydrochloride

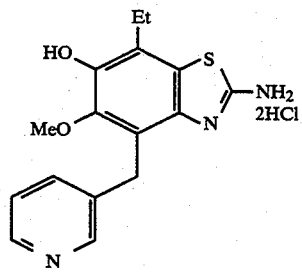

$^1$H-NMR(400 MHz,d$_6$-DMSO) δ (ppm): 1.11(t,3H,J=7.6 Hz), 2.62(q,2H,J=7.6 Hz), 3.64(s,3H), 4.35(s,2H), 7.92(dd,1H,J=8.0,5.6 Hz), 8.31(bd,1H,J=8.0 Hz), 8.73(d,1H,J=5.6 Hz), 8.77(bs,1H).

EXAMPLE 23

7-Ethyl-6-hydroxy-5-methoxy-2-methylamino-4-(3-pyridylmethyl)benzothiazole dihydrochloride

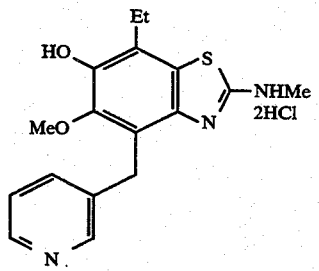

$^1$H-NMR(400 MHz,d$_6$-DMSO) δ (ppm): 1.09(t,3H,J=7.6 Hz), 2.60(q,2H,J=7.6 Hz), 2.94(s,3H), 3.66(s,3H), 4.38(s,2H), 7.13(s,1H), 7.25(s,1H), 7.38(s,1H), 7.94(dd,1H,J=8.0,5.6 Hz), 8.38(bd,1H,J=8.0 Hz), 8.73(d,1H,J=5.6 Hz), 8.82(bs,1H). Mass: FAB(Pos) m/z 330(M+H)+

What we claim is:

1. A benzothiazole derivative represented by the following formula (I):

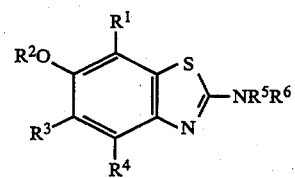

(I)

wherein R$^1$ is a group represented by the formula:

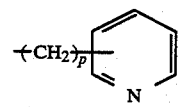

wherein p is an integer of from 1 to 4, or a group represented by the formula:

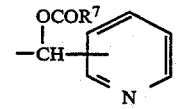

wherein R$^7$ represents a lower alkyl group;

R$^3$ represents a hydrogen atom, a lower alkyl group, a lower alkoxy group, a group represented by the formula:

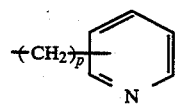

wherein p is an integer of from 1 to 4, or a group represented by the formula:

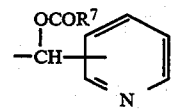

wherein R$^7$ represents a lower alkyl group;

R$^4$ represents a hydrogen atom, a lower alkyl group, a phenyl group, or a group represented by the formula:

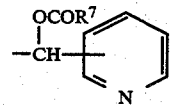

wherein R$^7$ represents a lower alkyl group, with the proviso that R$^3$ and R$^4$ are not both hydrogen atoms; or R$^3$ and R$^4$ may form a benzene ring together with the carbon atoms to which they are bound;

R$^2$ represents a hydrogen atom or a protective group of a hydroxyl group; and

R$^5$ and R$^6$ are either same or different and each represents a hydrogen atom, a lower alkyl group, a group represented by the formula:

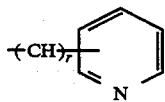

wherein r is an integer of from to 4, or an acyl group; or a pharmacologically acceptable salt thereof.

2. The benzothiazole derivative or a pharmacologically acceptable salt thereof as claimed in claim 1, wherein $R^3$ is a lower alkyl group.

3. The benzothiazole derivative or a pharmacologically acceptable salt thereof as claimed in claim 1, wherein $R^4$ is a lower alkyl group.

4. The benzothiazole derivative or a pharmacologically acceptable salt thereof as claimed in claim 1, wherein $R^1$ is a group represented by the formula:

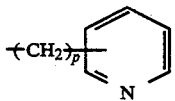

wherein p is an integer of from 1 to 4.

5. The benzothiazole derivative or a pharmacologically acceptable salt thereof as claimed in claim 1, wherein $R^3$ is a group represented by the formula:

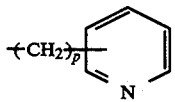

wherein p is an integer of from 1 to 4.

6. The benzothiazole derivative or a pharmacologically acceptable salt thereof as claimed in claim 1, wherein $R^2$ is a hydrogen atom.

7. The benzothiazole derivative or a pharmacologically acceptable salt thereof as claimed in claim 1, wherein one of $R^5$ and $R^6$ is a hydrogen atom while the other is a lower alkyl group.

8. The benzothiazole derivative or a pharmacologically acceptable salt thereof as claimed in claim 1, wherein one of $R^5$ and $R^6$ is a hydrogen atom while the other is a group represented by the following formula:

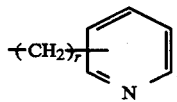

wherein r is an integer of from 1 to 4.

9. The benzothiazole derivative or a pharmacologically acceptable salt thereof as claimed in claim 1, wherein $R^3$, $R^4$ and $R^5$ are each a lower alkyl group, $R^1$ is a group represented by the formula:

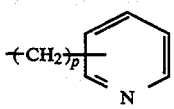

wherein p is an integer of from 1 to 4; and $R^2$ and $R^6$ are each a hydrogen atom.

10. The benzothiazole derivative or a pharmacologically acceptable salt thereof as claimed in claim 9, wherein $R^1$ is a 3-pyridylmethyl group.

11. A pharmacological composition which comprises a therapeutically effective amount of the benzothiazole derivative or a pharmacologically acceptable salt thereof as claimed in claim 1 and a pharmacologically acceptable vehicle.

12. A method for treating a disease in which 5-lipoxygenase activity is raised, comprising administering a pharmaceutically effective amount of the benzothiazole derivative or a pharmacologically acceptable salt thereof as claimed in claim 1 to a patient suffering from said disease in which the activity of the 5-lipoxygenase is raised.

13. A method for treating a disease in which thromboxane synthetase activity is raised; comprising administering a pharmaceutically effective amount of the benzothiazole derivative or a pharmacologically acceptable salt thereof as claimed in claim 1 to a patient suffering from said disease in which the activity of thromboxane synthetase is raised.

14. A method for treating a disease in which leukotriene synthesis is raised, comprising administering a pharmaceutically effective amount of the benzothiazole derivative or a pharmacologically acceptable salt thereof as claimed in claim 1 to a patient suffering from said disease in which the synthesis of leukotrienes is raised.

15. A method for treating a disease in which synthesis of thromboxanes is raised, comprising administering a pharmaceutically effective amount of the benzothiazole derivative or a pharmacologically acceptable salt thereof as claimed in claim 1 to a patient suffering from said disease in which the synthesis of thromboxanes is raised.

16. A method for treating inflammatory bowel diseases, comprising administering a pharmaceutically effective amount of the benzothiazole derivative or a pharmacologically acceptable salt thereof as claimed in claim 1 a patient suffering from said inflammatory bowel diseases.

17. A method for treating ulcerative coliris, comprising administering a pharmaceutically effective amount of the benzothiazole derivative or a pharmacologically acceptable salt thereof as claimed in claim 1 to a patient suffering from said ulcerative colitis.

18. The benzothiazole derivative as claimed in claim 1, wherein said benzothiazole derivative is 2-ethylamino-6-hydroxy-4,5-dimethyl-7-(3-pyridylmethyl) benzothiazole or a pharmacologically acceptable salt thereof.

* * * * *